US010201418B2

(12) United States Patent
Biadillah et al.

(10) Patent No.: US 10,201,418 B2
(45) Date of Patent: *Feb. 12, 2019

(54) VALVE REPLACEMENT DEVICES, DELIVERY DEVICE FOR A VALVE REPLACEMENT DEVICE AND METHOD OF PRODUCTION OF A VALVE REPLACEMENT DEVICE

(71) Applicant: SYMETIS SA, Ecublens VD (CH)

(72) Inventors: Youssef Biadillah, Lausanne (CH);
Stephane Delaloye, Bulach (CH);
Fabien Lombardi, Prilly (CH);
Jean-Luc Hefti, Cheseaux-Noreaz (CH)

(73) Assignee: SYMETIS, SA, Ecublens (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/143,166

(22) Filed: Apr. 29, 2016

(65) Prior Publication Data

US 2016/0317298 A1    Nov. 3, 2016

Related U.S. Application Data

(63) Continuation of application No. 13/821,476, filed as application No. PCT/EP2011/065744 on Sep. 12, 2011, now Pat. No. 9,333,075.

(30) Foreign Application Priority Data

Sep. 10, 2010    (EP) .................................... 10176281
Jan. 11, 2011    (EP) .................................... 11150544
(Continued)

(51) Int. Cl.
*A61F 2/24*    (2006.01)
*A61F 2/95*    (2013.01)

(52) U.S. Cl.
CPC .......... *A61F 2/2418* (2013.01); *A61F 2/2436* (2013.01); *A61F 2002/9505* (2013.01);
(Continued)

(58) Field of Classification Search
CPC ............................. A61F 2/241; A61F 2/24182
See application file for complete search history.

(56) References Cited

U.S. PATENT DOCUMENTS 15,192 A    6/1856    Peale
2,682,057 A    6/1954    Lord
(Continued)

FOREIGN PATENT DOCUMENTS

AU    2002329324 B2    7/2007
CN    1338951 A    3/2002
(Continued)

OTHER PUBLICATIONS

US 8,062,356, 11/2011, Salahieh et al. (withdrawn)
(Continued)

*Primary Examiner* — Thomas J Sweet
*Assistant Examiner* — Daniel Bissing
(74) *Attorney, Agent, or Firm* — Seager, Tufte & Wichkem LLP

(57) ABSTRACT

A device for heart valve replacement comprises a valve component having at least two valve leaflets preferably made of pericardium tissue. Each valve leaflet includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts generally aligned parallel to an axis
(Continued)

Figure 1:
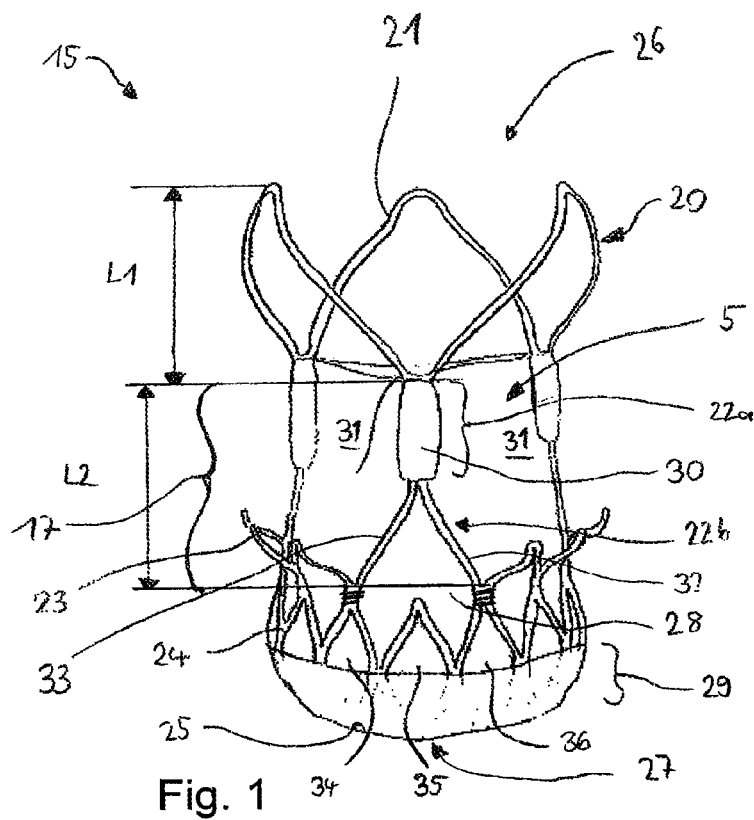

Fig. 1 spanning from the first end to the second end. The commissural posts are formed in the shape of a wishbone.

15 Claims, 5 Drawing Sheets

(30) Foreign Application Priority Data

May 15, 2011 (EP) .................................. 11004013
May 16, 2011 (EP) .................................. 11166201

(52) U.S. Cl.
CPC . *A61F 2220/0075* (2013.01); *A61F 2230/001* (2013.01); *A61F 2230/0013* (2013.01); *A61F 2250/0039* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,029,819 A | 4/1962 | Starks |
| 3,099,016 A | 7/1963 | Lowell |
| 3,113,586 A | 12/1963 | Edmark |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |

(56) References Cited

U.S. PATENT DOCUMENTS

| | | | |
|---|---|---|---|
| 5,360,444 | A | 11/1994 | Kusuhara |
| 5,370,685 | A | 12/1994 | Stevens |
| 5,389,106 | A | 2/1995 | Tower |
| 5,397,351 | A | 3/1995 | Pavcnik et al. |
| 5,409,019 | A | 4/1995 | Wilk |
| 5,411,552 | A | 5/1995 | Andersen et al. |
| 5,425,739 | A | 6/1995 | Jessen |
| 5,425,762 | A | 6/1995 | Muller |
| 5,431,676 | A | 7/1995 | Dubrul et al. |
| 5,443,446 | A | 8/1995 | Shturman |
| 5,443,449 | A | 8/1995 | Buelna |
| 5,443,477 | A | 8/1995 | Marin et al. |
| 5,443,495 | A | 8/1995 | Buscemi et al. |
| 5,443,499 | A | 8/1995 | Schmitt |
| 5,469,868 | A | 11/1995 | Reger |
| 5,476,506 | A | 12/1995 | Lunn |
| 5,476,510 | A | 12/1995 | Eberhardt et al. |
| 5,480,423 | A | 1/1996 | Ravenscroft et al. |
| 5,480,424 | A | 1/1996 | Cox |
| 5,489,297 | A | 2/1996 | Duran |
| 5,500,014 | A | 3/1996 | Quijano et al. |
| 5,507,767 | A | 4/1996 | Maeda et al. |
| 5,522,881 | A | 6/1996 | Lentz |
| 5,534,007 | A | 7/1996 | Germain et al. |
| 5,545,133 | A | 8/1996 | Burns et al. |
| 5,545,209 | A | 8/1996 | Roberts et al. |
| 5,545,211 | A | 8/1996 | An et al. |
| 5,545,214 | A | 8/1996 | Stevens |
| 5,549,665 | A | 8/1996 | Vesely et al. |
| 5,554,185 | A | 9/1996 | Block et al. |
| 5,571,174 | A | 11/1996 | Love et al. |
| 5,571,175 | A | 11/1996 | Vanney et al. |
| 5,571,215 | A | 11/1996 | Sterman et al. |
| 5,573,520 | A | 11/1996 | Schwartz et al. |
| 5,575,818 | A | 11/1996 | Pinchuk |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,784 | A | 5/1997 | Strecker |
| 5,645,559 | A | 7/1997 | Hachtrnan et al. |
| 5,653,745 | A | 8/1997 | Trescony et al. |
| 5,653,749 | A | 8/1997 | Love et al. |
| 5,662,671 | A | 9/1997 | Barbut et al. |
| 5,667,523 | A | 9/1997 | Bynon et al. |
| 5,674,277 | A | 10/1997 | Freitag |
| 5,681,345 | A | 10/1997 | Euteneuer |
| 5,693,083 | A | 12/1997 | Baker et al. |
| 5,693,088 | A | 12/1997 | Lazarus |
| 5,693,310 | A | 12/1997 | Gries et al. |
| 5,695,498 | A | 12/1997 | Tower |
| 5,709,713 | A | 1/1998 | Evans et al. |
| 5,713,951 | A | 2/1998 | Garrison et al. |
| 5,713,953 | A | 2/1998 | Vallana et al. |
| 5,716,370 | A | 2/1998 | Williamson, IV et al. |
| 5,716,417 | A | 2/1998 | Girard et al. |
| 5,720,391 | A | 2/1998 | Dohm et al. |
| 5,725,549 | A | 3/1998 | Lam |
| 5,728,068 | A | 3/1998 | Leone et al. |
| 5,733,325 | A | 3/1998 | Robinson et al. |
| 5,735,842 | A | 4/1998 | Krueger et al. |
| 5,749,890 | A | 5/1998 | Shaknovich |
| 5,755,783 | A | 5/1998 | Stobie et al. |
| 5,756,476 | A | 5/1998 | Epstein et al. |
| 5,769,812 | A | 6/1998 | Stevens et al. |
| 5,769,882 | A | 6/1998 | Fogarty et al. |
| 5,772,609 | A | 6/1998 | Nguyen et al. |
| 5,776,188 | A | 7/1998 | Shepherd et al. |
| 5,782,904 | A | 7/1998 | White et al. |
| 5,800,456 | A | 9/1998 | Maeda et al. |
| 5,800,531 | A | 9/1998 | Cosgrove et al. |
| 5,807,241 | A | 9/1998 | Heimberger |
| 5,807,405 | A | 9/1998 | Vanney et al. |
| 5,817,126 | A | 10/1998 | Imran |
| 5,824,037 | A | 10/1998 | Fogarty et al. |
| 5,824,041 | A | 10/1998 | Lenker et al. |
| 5,824,043 | A | 10/1998 | Cottone |
| 5,824,053 | A | 10/1998 | Khosravi et al. |
| 5,824,055 | A | 10/1998 | Spiridigliozzi et al. |
| 5,824,056 | A | 10/1998 | Rosenberg |
| 5,824,064 | A | 10/1998 | Taheri |
| 5,840,081 | A | 11/1998 | Andersen et al. |
| 5,843,158 | A | 12/1998 | Lenker et al. |
| 5,843,161 | A | 12/1998 | Solovay |
| 5,855,597 | A | 1/1999 | Jayaraman |
| 5,855,601 | A | 1/1999 | Bessler et al. |
| 5,855,602 | A | 1/1999 | Angell |
| 5,860,966 | A | 1/1999 | Tower |
| 5,860,996 | A | 1/1999 | Urban et al. |
| 5,861,024 | A | 1/1999 | Rashidi |
| 5,861,028 | A | 1/1999 | Angell |
| 5,868,783 | A | 2/1999 | Tower |
| 5,876,419 | A | 3/1999 | Carpenter et al. |
| 5,876,448 | A | 3/1999 | Thompson et al. |
| 5,885,228 | A | 3/1999 | Rosenman et al. |
| 5,888,201 | A | 3/1999 | Stinson et al. |
| 5,891,191 | A | 4/1999 | Stinson |
| 5,895,399 | A | 4/1999 | Barbut et al. |
| 5,906,619 | A | 5/1999 | Olson et al. |
| 5,907,893 | A | 6/1999 | Zadno-Azizi et al. |
| 5,910,154 | A | 6/1999 | Tsugita et al. |
| 5,911,734 | A | 6/1999 | Tsugita et al. |
| 5,925,063 | A | 7/1999 | Khosravi |
| 5,944,738 | A | 8/1999 | Amplatz et al. |
| 5,954,766 | A | 9/1999 | Zadno-Azizi et al. |
| 5,957,949 | A | 9/1999 | Leonhardt et al. |
| 5,968,070 | A | 10/1999 | Bley et al. |
| 5,984,957 | A | 11/1999 | Laptewicz et al. |
| 5,984,959 | A | 11/1999 | Robertson et al. |
| 5,989,280 | A | 11/1999 | Euteneuer et al. |
| 5,993,469 | A | 11/1999 | McKenzie et al. |
| 5,997,557 | A | 12/1999 | Barbut et al. |
| 6,010,522 | A | 1/2000 | Barbut et al. |
| 6,015,431 | A | 1/2000 | Thornton et al. |
| 6,022,370 | A | 2/2000 | Tower |
| 6,027,520 | A | 2/2000 | Tsugita et al. |
| 6,027,525 | A | 2/2000 | Suh et al. |
| 6,042,598 | A | 3/2000 | Tsugita et al. |
| 6,042,607 | A | 3/2000 | Williamson, IV et al. |
| 6,051,014 | A | 4/2000 | Jang |
| 6,059,827 | A | 5/2000 | Fenton |
| 6,074,418 | A | 6/2000 | Buchanan et al. |
| 6,093,203 | A | 7/2000 | Uflacker |
| 6,096,074 | A | 8/2000 | Pedros |
| 6,110,198 | A | 8/2000 | Fogarty et al. |
| 6,123,723 | A | 9/2000 | Konya et al. |
| 6,132,473 | A | 10/2000 | Williams et al. |
| 6,139,510 | A | 10/2000 | Palermo |
| 6,142,987 | A | 11/2000 | Tsugita |
| 6,146,366 | A | 11/2000 | Schachar |
| 6,162,245 | A | 12/2000 | Jayaraman |
| 6,165,200 | A | 12/2000 | Tsugita et al. |
| 6,165,209 | A | 12/2000 | Patterson et al. |
| 6,168,579 | B1 | 1/2001 | Tsugita |
| 6,168,614 | B1 | 1/2001 | Andersen et al. |
| 6,171,327 | B1 | 1/2001 | Daniel et al. |
| 6,171,335 | B1 | 1/2001 | Wheatley et al. |
| 6,179,859 | B1 | 1/2001 | Bates et al. |
| 6,187,016 | B1 | 2/2001 | Hedges et al. |
| 6,197,053 | B1 | 3/2001 | Cosgrove et al. |
| 6,200,336 | B1 | 3/2001 | Pavcnik et al. |
| 6,206,911 | B1 | 3/2001 | Milo |
| 6,214,036 | B1 | 4/2001 | Letendre et al. |
| 6,221,006 | B1 | 4/2001 | Dubrul et al. |
| 6,221,091 | B1 | 4/2001 | Khosravi |
| 6,221,096 | B1 | 4/2001 | Alba et al. |
| 6,221,100 | B1 | 4/2001 | Strecker |
| 6,231,544 | B1 | 5/2001 | Tsugita et al. |
| 6,231,551 | B1 | 5/2001 | Barbut |
| 6,241,757 | B1 | 6/2001 | An et al. |
| 6,245,102 | B1 | 6/2001 | Jayaraman |
| 6,251,135 | B1 | 6/2001 | Stinson et al. |
| 6,258,114 | B1 | 7/2001 | Onya Et Al |
| 6,258,115 | B1 | 7/2001 | Ubrul |

(56) References Cited

U.S. PATENT DOCUMENTS

| | | |
|---|---|---|
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Orikawa et al. |
| 6,508,833 B2 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |

(56) References Cited

U.S. PATENT DOCUMENTS

| | | |
|---|---|---|
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,278 B2 | 2/2008 | Seguin et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,473,417 B2 | 1/2009 | Zeltinger et al. |
| 7,491,232 B2 | 2/2009 | Bolduc et al. |
| 7,510,574 B2 | 3/2009 | Lê et al. |
| 7,510,575 B2 | 3/2009 | Spenser et al. |
| 7,524,330 B2 | 4/2009 | Berreklouw |
| 7,530,995 B2 | 5/2009 | Quijano et al. |
| 7,544,206 B2 | 6/2009 | Cohn |
| 7,601,159 B2 | 10/2009 | Ewers et al. |
| 7,622,276 B2 | 11/2009 | Cunanan et al. |
| 7,628,802 B2 | 12/2009 | White et al. |
| 7,628,803 B2 | 12/2009 | Pavcnik et al. |
| 7,632,298 B2 | 12/2009 | Hijikema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,914,574 B2 | 3/2011 | Schmid et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,512,394 B2 | 8/2013 | Schmid et al. |
| 8,523,936 B2 | 9/2013 | Schmid et al. |
| 8,540,762 B2 | 9/2013 | Schmid et al. |
| 8,545,547 B2 | 10/2013 | Schmid et al. |
| 8,579,962 B2 | 11/2013 | Salahieh et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,743 B2 | 4/2014 | Holecek et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |

(56) References Cited

U.S. PATENT DOCUMENTS

| | | |
|---|---|---|
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0177894 A1 | 11/2002 | Acosta |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212447 A1 | 11/2003 | Euteneuer et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Dugan et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2005/0010287 A1 | 1/2005 | Macoviak et al. |
| 2005/0021136 A1 | 1/2005 | Kie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |

(56) References Cited

U.S. PATENT DOCUMENTS

| | | |
|---|---|---|
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yarnit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025844 A1 | 2/2006 | Majercak et al. |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0282157 A1 | 12/2006 | Hill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0088431 A1 | 4/2007 | Bourang et al. |
| 2007/0100427 A1 | 5/2007 | Perouse |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0233222 A1 | 10/2007 | Roeder et al. |
| 2007/0244552 A1 | 10/2007 | Salahieh et al. |
| 2007/0270944 A1 | 11/2007 | Bergheim et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071361 A1 | 3/2008 | Tuval et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0099554 A1 | 4/2009 | Forster et al. |
| 2009/0171456 A1 | 7/2009 | Kveen et al. |
| 2009/0216312 A1 | 8/2009 | Straubinger et al. |
| 2009/0222076 A1 | 9/2009 | Figulla |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0082094 A1 | 4/2010 | Quadri et al. |
| 2010/0094399 A1 | 4/2010 | Dorn et al. |
| 2010/0100167 A1 | 4/2010 | Bortlein et al. |
| 2010/0121434 A1 | 5/2010 | Paul et al. |
| 2010/0161045 A1 | 6/2010 | Righini |
| 2010/0168834 A1 | 7/2010 | Ryan et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0268332 A1 | 10/2010 | Tuval et al. |
| 2010/0280495 A1 | 11/2010 | Paul et al. |
| 2010/0298931 A1 | 11/2010 | Quadri et al. |

(56) References Cited

U.S. PATENT DOCUMENTS

| | | |
|---|---|---|
| 2011/0040366 A1 | 2/2011 | Goetz et al. |
| 2011/0066224 A1 | 3/2011 | White |
| 2011/0098805 A1 | 4/2011 | Dwork et al. |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0179244 A1 | 7/2012 | Schankereli et al. |
| 2012/0197379 A1 | 8/2012 | Laske et al. |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0123796 A1 | 5/2013 | Sutton et al. |
| 2013/0138207 A1 | 5/2013 | Quadri et al. |
| 2013/0158656 A1 | 6/2013 | Sutton et al. |
| 2013/0166017 A1 | 6/2013 | Cartledge et al. |
| 2013/0184813 A1 | 7/2013 | Quadri et al. |
| 2013/0190865 A1 | 7/2013 | Anderson |
| 2013/0253640 A1 | 9/2013 | Meiri et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0200649 A1 | 7/2014 | Essinger et al. |
| 2014/0243967 A1 | 8/2014 | Salahieh et al. |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |
| 2016/0045307 A1 | 2/2016 | Yohanan et al. |
| 2016/0199184 A1 | 7/2016 | Ma et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 202010007592 U1 | 10/2010 |
| EP | 0103546 B1 | 8/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1690515 A1 | 8/2006 |
| EP | 1605871 B1 | 7/2008 |
| EP | 2033593 A1 | 3/2009 |
| EP | 2047824 B1 | 5/2012 |
| EP | 2474287 A1 | 7/2012 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| JP | 2010528761 A | 8/2010 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9415549 A1 | 7/1994 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |

(56) References Cited

FOREIGN PATENT DOCUMENTS

| | | |
|---|---|---|
| WO | 0135870 A1 | 5/2001 |
| WO | 0149213 A2 | 7/2001 |
| WO | 0162189 A1 | 8/2001 |
| WO | 01054625 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 3205885 A2 | 1/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2006093795 A1 | 9/2006 |
| WO | 2007005799 A1 | 1/2007 |
| WO | 2007009117 A1 | 1/2007 |
| WO | 2007035471 A2 | 3/2007 |
| WO | 2005102015 A3 | 4/2007 |
| WO | 2006138391 A2 | 4/2007 |
| WO | 2007044285 A2 | 4/2007 |
| WO | 2007058847 A2 | 5/2007 |
| WO | 2007071436 A2 | 6/2007 |
| WO | 2007092354 A2 | 8/2007 |
| WO | 2007097983 A2 | 8/2007 |
| WO | 2007053243 A2 | 9/2007 |
| WO | 2007033093 A2 | 1/2008 |
| WO | 2008028569 A1 | 3/2008 |
| WO | 2008035337 A2 | 3/2008 |
| WO | 2008150529 A1 | 12/2008 |
| WO | 2009002548 A1 | 12/2008 |
| WO | 2009024859 A2 | 2/2009 |
| WO | 2009042196 A2 | 4/2009 |
| WO | WO 2009053497 A1 * 4/2009 ........... A61F 2/2418 |
| WO | 2009091509 A1 | 7/2009 |
| WO | 2009149462 A2 | 12/2009 |
| WO | 2010042950 A2 | 4/2010 |
| WO | 2010045297 A2 | 4/2010 |
| WO | 2010098857 A1 | 9/2010 |
| WO | 2011025945 A1 | 3/2011 |
| WO | 2011051043 A1 | 5/2011 |
| WO | 2012009006 A1 | 1/2012 |
| WO | 2012032187 A1 | 3/2012 |
| WO | 2012038550 A1 | 3/2012 |
| WO | 2012095455 A2 | 7/2012 |
| WO | 2012116368 A2 | 8/2012 |
| WO | 2012150290 A1 | 11/2012 |
| WO | 2012162228 A1 | 11/2012 |
| WO | 2013009975 A1 | 1/2013 |
| WO | 2013028387 A2 | 2/2013 |
| WO | 2013074671 A1 | 5/2013 |
| WO | 2013096545 A1 | 6/2013 |
| WO | 2016126511 A2 | 8/2016 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)
International Search Report for International Application No. PCT/EP2011/065744, dated Feb. 17, 2012.
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EpP Patent Office, EP Application No. 04813777.2, Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Nashington DC, v-13, http://www.nap.edu/catalog/117521a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in be aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May, 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.

(56) References Cited

OTHER PUBLICATIONS

Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent—Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." the Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Carpentier-Edwards Perimount Bioprosthesis (2003).
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. Of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17)II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).

Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Fluency Vascular Stent Graft Instructions for Use (2003).
Sore Excluder Instructions for Use (2002).
Greenberg, "Abdominal Aortic Endografting: Fixation and Sealing." J. Am. Coll. Surg. 194:1:S79-S87 (2002).
Gross!, "Impact of Minimally Invasive Valvular Heart Surgery: A Case-Control Study." Ann. Thorac. Surg., 71:807-10 (2001).
Helmus' "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. college of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 154-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Zhou et al., "Self-expandable Valved Stent of Large Size: Off-Bypass Implantation in Pulmonary Position." Fur. J. Cardiothorac, 24: 212-216, Aug. 2003.
EP Patent Application No. 11150544.2, (opposed patent) Certificate from EPO, 128 pages, dated Nov. 1, 2011.
EP Patent Application No. 10176281.3, Certificate from EPO, 13 pages, dated Oct. 9, 2010.
EP Patent Application No. 11150544.2, Certificate from EPO, 35 pages, dated Nov. 1, 2011.
EP Patent Application No. 11166201.1, Certificate from EPO, 40 pages, dated Nov. 5, 2016.
"Feature Analysis of EP2613737B1" Jul. 25, 2018.
EP Patent Application No. Certificate from EPO, 38 pages, dated May 15, 2011.
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "Mycobacterium Chelonei Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.

(56) References Cited

OTHER PUBLICATIONS

Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
McKay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," Asaio J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5 (6):491-9 (1991).
Pavcnik et al., "Percutaneous Bioprosthetic Venous Valve: A Long-term Study in Sheep." J. of Vascular Surg., 35(3): 598-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. 4/99.
Provisional U.S. Appl. No. 60/553,945, Jennifer K. White, "Prosthetic Valve With Dynamic Seal", pp. 1-43, Mar. 18, 2004.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radio!. 15: 319-327 (1992).
Schurink et al,. "Stent Attachment Site—related Endoleakage after Stent Graft Treatment: An in vitro study of the affects of graft size, stent type, and atherosclerotic wall changes." J. Vase. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).
Stassano, "Mid-term Results of the Valve-on-Valve Technique for Bioprosthetic Failure." European Journal of Cardiothoracic Surgery: vol. 18, 453-457, Oct. 2000.
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).
Thompson et al., "Endoluminal stent grafting of the thoracic aorta: Initial experience with the Gore Excluder," Journal of Vascular Surgery, 1163-70 (Jun. 2002).
Topol, "Percutaneous Expandable Prosthetic Valves." Textbook of Interventional Cardiology, W.B. Saunders Company, 2: 1268-1276, 1994.
USPTO Case IPR 2017-0006, U.S. Pat. No. 8,992,608 B2, "Final Written Decision" dated Mar. 23, 2018.
USPTO Case IPR2016, U.S. Pat. No. 8,992,608 "Petition for Interpartes Review of U.S. Patent No. 8,992,608" dated Oct. 12, 2016.
USPTO Case IPR2017-01293, U.S. Pat. No. 8,992,608 B, dated Oct. 13, 2017.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProffies, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).

\* cited by examiner

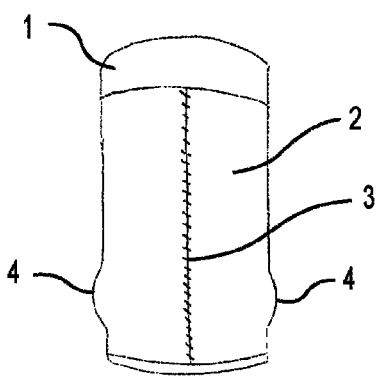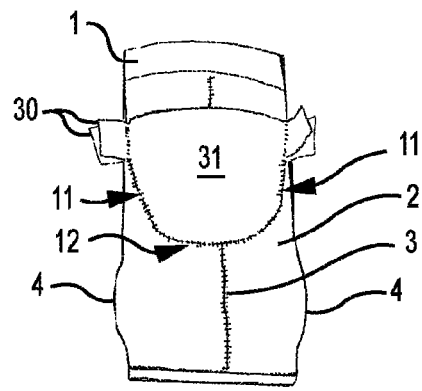
Fig. 5a  Fig. 5b
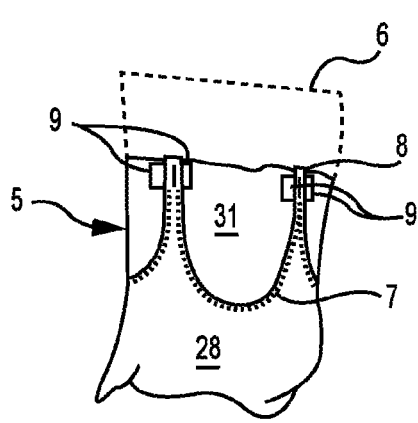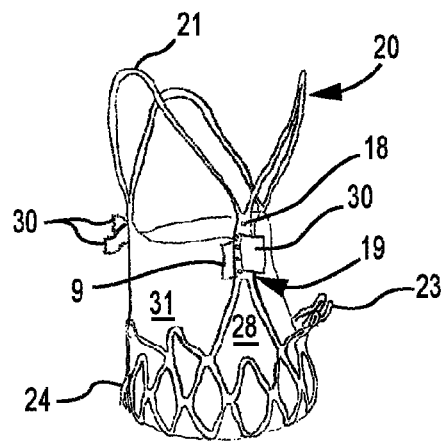
Fig. 5c  Fig. 5d
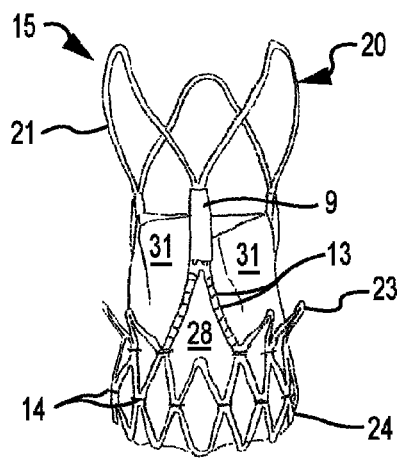
Fig. 5e

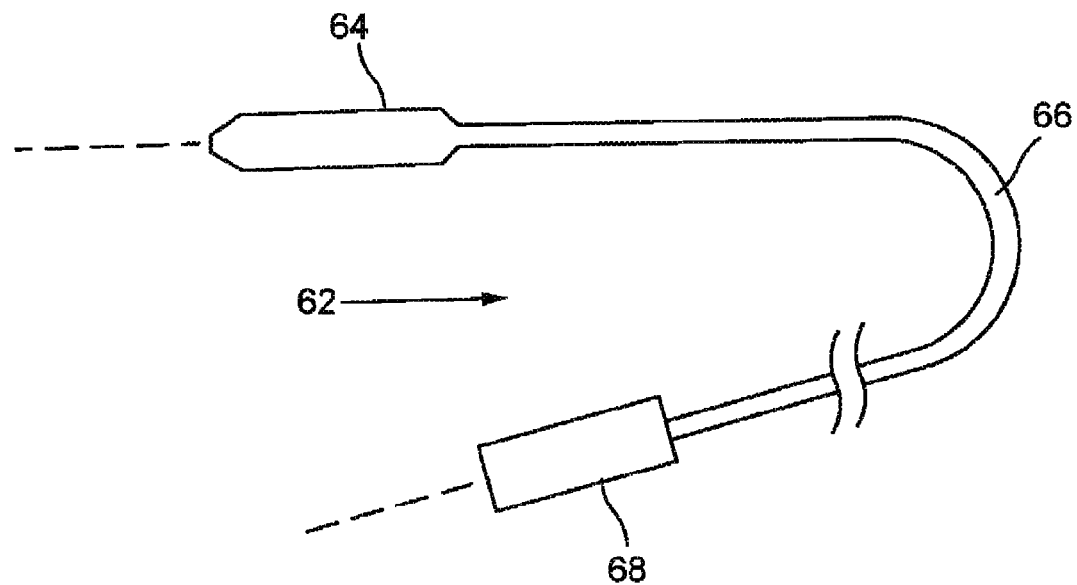
FIG. 7
FIG. 8
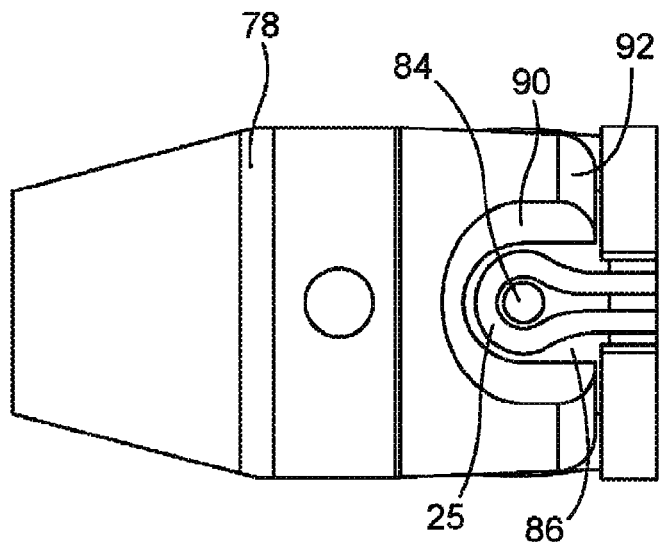
FIG. 9
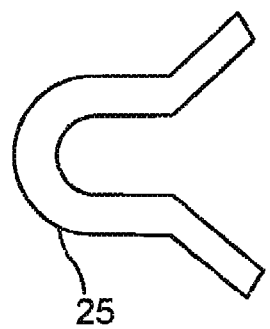

VALVE REPLACEMENT DEVICES, DELIVERY DEVICE FOR A VALVE REPLACEMENT DEVICE AND METHOD OF PRODUCTION OF A VALVE REPLACEMENT DEVICE

CROSS REFERENCE TO RELATED APPLICATIONS

This application is a continuation of and claims priority to U.S. application Ser. No. 13/821,476, filed Oct. 3, 2013, and entitled "Valve Replacement Devices, Delivery Device for a Valve Replacement Device and Method of Production of a Valve Replacement Device," which in turn claims priority to International Patent Application No. PCT/EP2011/065744, filed Sep. 12, 2011, and entitled "Valve Replacement Devices, Delivery Device for a Valve Replacement Device and Method of Production of a Valve Replacement Device," which claims priority to European Patent Application No. 10176281.3, filed Sep. 10, 2010, European Patent Application No. 11150544.2, filed Jan. 11, 2011, European Patent Application No. 11004013.6, filed May 15, 2011, and European Patent Application No. 11166201.1, filed May 16, 2011. The present application incorporates herein by reference the disclosures of each of the above-referenced applications in their entireties.

The present invention is directed to devices for valve replacement, especially of the aortic valve. Further, the present invention is also related to a delivery device for a valve replacement device and to a method of production of a valve replacement device. Valve replacement devices may also be referred to a stent-valves or valved-stents.

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to establish a less invasive cardiac valve replacement procedure, by delivering and implanting a cardiac replacement valve via a catheter inserted through a smaller skin incision via either a transvascular approach—delivering the new valve through the femoral artery, or by transapical route, where the replacement valve is delivered between ribs and directly through the wall of the heart to the implantation site.

Stent valves and delivery systems for placing a replacement valve via a catheter are known in the art, and are disclosed for example in WO 2007/071436 and WO 2009/053497.

Some known stents are made from a shape memory material, such as Nitinol, and are self-expanding. The valves may be from animals, for example porcine aortic valves. Alternatively the valves may at least partly be made of synthetic material, such as Dacron.

For example, the WO 2007/071436 discloses a valve replacement device comprising a valve element and a stent element. The stent element includes three different sections, wherein one section houses the valve element. The valve element includes three leaflets, which may be made of biological or artificial material. The three different sections may be provided with different diameters.

One major drawback of some known replacement valve stents is that even in a collapsed (crimped) state their diameter is often too big for transvascular delivery of the stent. Transfemoral delivery of the stent, where the stent has to be advanced over the aortic arch, requires even smaller diameters of less than 18 French (6 mm). Such small diameters may also be useful in transapical delivery if a smaller skin incision and/or smaller cut in the heart wall may be used.

Crimping some known stent valves to a diameter of less than 18 French would produce high strains on the replacement valve, which may lead to damages.

Thus there is a need for replacement valve devices, which avoid the disadvantages of the known and which in particular may be crimped to small diameters without the risk of damaging the replacement valves and which may be reliably placed and tightly anchored over an aortic annulus.

Aspects of the invention are defined in the claims.

Broadly speaking, one aspect of the invention provides a device for heart valve replacement, comprising a valve component (and/or a tissue valve) with at least two valve leaflets. The term "valve component" is used herein to refer to the leaflets collectively, whether or not the leaflets are secured together to define a unitary valve structure independent of other components.

The leaflets are preferably made of pericardium tissue, most preferably from porcine pericardium tissue or bovine pericardium. Porcine pericardium may be desirably thin and sufficiently durable. Bovine pericardium may be thicker and even more durable when this is desired. Each valve leaflet includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts optionally and/or generally aligned parallel to an axis spanning from the first end to the second end. The tabs of the leaflets are directly attached to the commissural posts, preferably to attachment means provided on said commissural posts.

The valve leaflets are configured and dimensioned such as to form a replacement valve. In some embodiments, the leaflets have a straight or slightly curved upper free edge, two lateral edges and a substantially arcuate lower edge. At least one tab is arranged on each lateral edge, preferably in the area of the upper free edge of the leaflet. In the valve replacement device, the at least two leaflets are positioned such that their upper free edges may be pressed together to prevent blood flow in one direction, e.g. towards the heart during diastole in the case of an aortic valve replacement, and move apart to allow blood flow in the other direction, e.g. away of the heart during systole.

More preferably, three valve leaflets are provided. This allows to mimic the natural tricuspid valve architecture e.g. of the aortic, pulmonary, tricuspid or mitral valve. Alternatively, the valve replacement device may also comprise more leaflets, such as four, five or more.

While it is known to use a large selection of different artificial materials for replacement valves, it is preferred that the at least two leaflets of the valve replacement device according to the present invention are made of pericardium tissue. Most preferably, the at least two leaflets are made from porcine pericardium tissue. Pericardium tissue is sufficiently thin and yet durable enough to be used as leaflet material. The porcine heart shows a lot of similarities to the human heart. Therefore it is advantageous to use porcine pericardium tissue. Further, porcine pericardium tissue is readily available. For the present invention, the use of a porcine aortic valve is not indicated, since it is too thick and would not allow the crimping of the valve replacement device to less than 20 French. As mentioned previously, bovine pericardium may also be used for the leaflets where even greater durability is desired, optionally at the expense of thicker tissue.

The stent component preferably is of the self-expanding type. Such stents are known in the art and often comprise or are made of a shape-memory material, such a Nitinol. Alternatively, the stent component may be made of or comprise a plastically deformable material and may be expanded to the functional state by external means, such as a balloon catheter.

In the compressed, e.g., the crimped state, the stent component may be inserted in the area of a heart valve of a patient, such as the aortic valve. Further, the diameter of the stent component in the compressed state is such that it may be advanced into a patient's heart through an artery, such as the femoral artery. The diameter and/or the flexibility of the stent component in the compressed state are therefore preferably such that the valve replacement device may be advanced through the aortic arch.

In the functional state, the stent component is in an at least partly expanded, or non-compressed configuration. Optionally, the stent component defines an interior conduit space. The conduit space may be generally cylindrical and/or tubular. The valve leaflets are arranged to span the interior space within the stent component. Once the valve replacement device is positioned at a target position close to the natural valve of a patient, the stent component is expanded to its functional state. Preferably the stent component may additionally comprise anchoring elements which allow a secure attachment of the device within a cardiovascular vessel upon expansion of the stent element.

The natural valve leaflets of the patient may be pushed aside by the expanding stent component. Once fully expanded, the valve component arranged within the stent component will take over the function of the natural valve.

The stent component preferably comprises a first end, a second end and at least one intermediate section arranged between said first and said second end. The valve component is thereby preferably arranged within said intermediate section of the stent component. Optionally, the stent component is configured such that said intermediate section includes a conical and/or cylindrical conduit space, optionally with a constant diameter, said diameter most preferably being in the range of 15 mm to 35 mm. The length of said intermediate section thereby preferably is in the range of 10 mm to 50 mm.

In the functional state, said first and said second ends define inflow and outflow openings through or around which blood may flow in use. A simple embodiment of a valve replacement device according to the present invention may comprise only the intermediate section including a first and a second end. However, more preferably a valve replacement device according to the present invention comprises at least an additional inflow and/or an additional outflow section arranged between said intermediate section and said first and/or said second end.

"Inflow section" as understood herein is the section of the stent component where blood enters into said conduit space and/or the section of the stent component that, in use, is upstream of the valve leaflets; for example, in the case of a semilunar and/or aortic valve, the section of the stent component which is oriented towards the ventricle.

Accordingly, an "outflow section" as understood herein is the section of the stent component where blood leaves said conduit space and/or the section of the stent component that, in use, is downstream of the valve leaflets; for example, the section which is located in the artery for semilunar valves.

Said inflow and said outflow section may thereby have the same length or have different lengths. Further, said inflow and/or said outflow section may define a generally tubular conduit interior conduit space. The conduit space may be generally cylindrical. More preferably, said inflow and/or said outflow section include a generally conical conduit, i.e. a conduit with an increasing or a decreasing diameter. Alternatively, the inflow and the outflow section may include an interior conduit space of any appropriate geometric shape.

Optionally, said inflow and said outflow section may have the same maximal diameter or varying maximal diameters. A "maximal diameter" as understood herein is the largest diameter within such a section. Optionally, said inflow section has a smaller maximal diameter than said outflow section. Further, said intermediate section has a diameter which is smaller than the maximal diameter of either of said inflow or said outflow section. Most preferably said inflow and said outflow sections have a diameter which increases in the direction of said first and said second end. Alternatively, further sections may be arranged between said inflow and/or said outflow section and said intermediate section.

In a preferred embodiment, the inflow section has a maximal diameter in the range from 20 mm to 35 mm and the outflow section has a maximal diameter in the range from 20 mm to 55 mm.

The stent component may further comprise a lower anchoring crown. The lower anchoring crown may define an at least partly conical body. Said lower anchoring crown preferably is located between the second end and the intermediate section of the stent component and preferably configured as to be placed within the annulus and/or extend to the ventrical side of the annulus.

Additionally, the stent component may further comprise an upper anchoring crown in communication with or adjacent to the lower anchoring crown. The upper anchoring crown may define an at least partly conical body. Said conical body of said lower anchoring crown may slope outwardly in the direction of the second end and the conical body of the upper anchoring crown may slope outwardly in the direction of the intermediate section, e.g. such as to be placed on the aortic side of the annulus.

Preferably, the stent component further includes stabilization arches which are in communication with the commissural posts and extend towards the first end. The stabilization arches are preferably configured to engage the ascending aorta to orient the stent component longitudinally within the aorta or the aortic annulus, thus tending to correct any tilting of the stent component, with respect to the ascending aorta, during implantation. The commissural posts are thereby connected to each other through the stabilization arches, whereby two adjacent commissural posts are in connection with each other by means of one stabilization arch. Further, the commissural posts preferably are also in communication with the upper anchoring crown and/or the lower anchoring crown.

Further, the stent component preferably comprises at least one attachment element for mating engagement with a delivery device (for example, a stent holder of the delivery device). The at least one attachment element may be configured for restraining axial displacement of the stent component until the stent component is fully released. In some embodiments, the at least one attachment is provided at the lower crown, such that the ventrical part and/or inflow section of the valve replacement device is the last part to expand during placement of the device. The stent component may comprise any suitable number of attachment elements, for example, two, three, or more. The attachment elements may be spaced substantially uniformly in the circumferential direction.

Optionally, the at least one attachment element may comprise a U-shape portion joining two stent struts. The term U-shape is used herein to include any shape including a generally arcuate apex, whether or not the sides are straight or curved, bulged outwardly, parallel or non-parallel. In a collapsed (e.g. compressed) state of the stent when received within the accommodation region of the delivery catheter, the struts may lie adjacent each other at the attachment element, such that the arc of the U-shape portion extends around a first angle more than 180 degrees to define, for example, a closed or near closed (e.g. horseshoe shape) eyelet having an aperture larger than the spacing of the struts. The horseshoe shape of the eyelet aperture and the adjacent space between the struts may together define a keyhole type shape. In an expanded (or non-collapsed) state of the stent when released from the accommodation region of the delivery catheter, the struts may move apart, and the arc of the U-shape portion may extend around a second angle that is less than the first angle, to at least partly open the eyelet further. For example, the second angle may be about 180 degrees or less. In the expanded state, the attached element may define a substantially straight-sided U-shape with an arcuate apex.

The delivery catheter may comprise a sent-holder provided within a stent accommodation region. The stent-holder may comprise (i) a respective projection receivable within each eyelet. The projection may be dimensioned such that, when the stent component is in its collapsed state, the projection is trapped within the eyelet and unable to pass between the adjacent struts, and/or (ii) one or more recesses or interstices for accommodating the attachment element substantially therewithin, at least in the collapsed state of the stent component.

The above forms can provide for a compact, yet reliable and self-opening and/or self-releasing attachment between a stent-valve and a delivery system. The provision of the attachment elements also does not impede compressing of the stent component to a desirably small size.

In some embodiments, the intermediate section comprises at least two commissural posts generally aligned parallel to an axis spanning from the first end to the second end. The tabs of the leaflets are directly attached to said commissural posts, preferably to attachment means provided on said commissural posts.

The direct attachment of said leaflets to said commissural posts provides a high strain resistance of the leaflets. Optionally, in comparison to valve replacement stents as known in the art, the direct attachment of the leaflets to the commissural posts may optionally reduce the thickness of the crimped stent element, if excess layers of tissue between the leaflets and the commissural posts capable of withstanding the strain resistance may be avoided.

According to another aspect of the present invention, a device for heart valve replacement is provided which comprises a valve component and/or tissue valve having at least two valve leaflets. Said at least two valve leaflets are preferably made of pericardium tissue, most preferably porcine pericardium tissue. Each of said at least two valve leaflets includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts generally aligned parallel to an axis spanning from the first end to the second end. Said commissural posts are formed in the shape of a wishbone and said tabs are directly attached to said commissural posts, preferably to attachment means provided on said commissural posts.

A wishbone is generally shaped like an inverted letter "Y". The commissural posts therefore include two inclined legs (also referred to sometimes as arms) and one stem. The inclined legs may be straight, but preferably the two inclined legs are curved (e.g. around the axis of the stent component and/or in a circumferential plane). The shape, whether straight or curved, is preferably selected such that the legs of the wishbone are substantially in register and/or congruent with the lateral edges of the valve leaflets. This allows the commissural post to provide good support to the lateral edges of the valve leaflets. The lateral edges of the valve leaflets may be attached to the legs, and/or to inner skirt material between the leaflets and the commissural posts. The legs are thereby shaped such as to match generally the contour of the lateral edges of the leaflets. This allows the attachment of the lateral edges of the leaflets directly or indirectly to the legs of the wishbone shaped commissural posts, e.g. by means of a suture, for close support of the leaflets.

The configuration of other elements of this embodiment of a stent valve replacement device is similar to the ones described for the first embodiment above.

The commissural posts preferably comprise attachment means for the tabs of the valve leaflets, said attachment means including at least one opening adapted for the insertion of at least one tab.

Said openings are preferably configured as through holes, i.e. the openings are bounded and/or flanked on all sides by the commissural posts. Alternatively, said openings may also be configured as channel slits, i.e. bounded and/or flanked by the commissural posts only on three sides, while one side is open. The openings may be in any suitably form, like rectangular, round, oval, etc. Most preferably the openings are in the form of a long-hole. The openings are further adapted such that at least one tab of said valve leaflets may be inserted therethrough. Therefore the position of the openings on the commissural posts as well as their size is selected such that at least one tab of a valve leaflet may be inserted. Preferably said openings are adapted such that two tabs, e.g. from two neighbouring valve leaflets, may be inserted. Alternatively, the commissural posts may include more than one such openings. In this way, attachment of valve leaflets having more tabs, such as two tabs on each lateral edge, may be attached to said commissural posts. In a further alternative, the commissural posts may include two openings arranged parallel to each other, such that tabs of neighbouring valve leaflets may each be inserted into a separate opening. The tabs are preferably inserted into an opening, folded back over the commissural post towards the valve leaflet and sutured thereto.

Said attachment means may additionally include at least two bores adapted for the insertion of a suture wire, said bores preferably being in the form of round-bores. Provision of such additional bores facilitates the attachment of said tabs and/or of the lateral edges of the leaflets to said commissural posts. These additional at least two bores are preferably provided flanking said at least one opening.

The stent component preferably comprises a substantially parallel and/or non-parallel tubular portion arranged between said intermediate section and said second end, said tubular portion having a lattice structure of at least one row of cells, the wishbone shape of each commissural post spanning a respective sequence of at least three adjacent cells, such that the wishbone extends from outer cells of the sequence without attachment to the at least one intermediate cell of the sequence. Such an arrangement provides for ease of compression, while allowing the wishbone legs to have sufficient divergence to match the shape of the lateral edges of the leaflets.

In some embodiments, the legs of the wishbone are joined to the outer cells of the sequence in the lattice structure, therefore allowing the commissural post to span over at least three adjacent cells without being attached to the at least one intermediate cell. Alternatively, each commissural post may be configured to span over more than three adjacent cells, such as four, five, etc. Further alternatively, each commissural post may be configured to span a different number of adjacent cells. Preferably, the stems of the wishbone shaped commissural posts are in communication with each other by means of stabilization arches. The stems of two adjacent wishbone shaped commissural posts are thereby in communication with each other by means of one stabilization arch.

The valve replacement device additionally may comprise an inner skirt, preferably made of pericardium tissue, and attached to the leaflets. The inner skirt may serve to channel blood within the conduit space of the stent component, and obstruct leakage of blood through interstices of the stent component (e.g. through cells of a lattice structure).

In some embodiments, the inner skirt may have commissural portions spaced apart by scalloped clearances (e.g. scalloped cutouts). Each clearance is spanned by a respective valve leaflet. The lateral edges and/or lower edges of the leaflets may be attached to the inner skirt, for example, by sutures.

In some embodiments, the inner skirt may extend towards said second end, said skirt preferably being sutured to said stent device. Said skirt preferably covers at least partly an interior surface of the stent component. This reduces the occurrence of turbulent flow of the blood which may be triggered by the material of the stent component. Said skirt preferably is further sutured to said at least two valve leaflets.

Additionally, at least one section of said stent component is at least partially covered on the outside by an outer skirt.

The stent component is preferably configured such that when the valve replacement device in the compressed state is inserted into the sheath of a delivery device, such as a catheter, the aggregated diameter of the delivery device and the sheath is less than 20 French, preferably less than 18 French. This allows the insertion of the valve replacement device along an artery, preferably the femoral artery or the subclavian artery. It may also enable the valve replacement device to be inserted transapically using a small skin incision and/or cut through the heart wall.

According to yet another aspect of the invention there is provided a device for heart valve replacement comprising a valve component and/or tissue valve, including at least two valve leaflets each having at least two tabs. The at least two leaflets may be attached to an annular skirt on the inside of the skirt. The term "annular" as used herein is meant to designate a circumferentially running structure and is not limited to an exactly circular or ring like structure. A portion of the skirt material wraps at least partially around the commissural post without passing through the tab opening.

According to still another aspect of the invention there is provided a device for heart valve replacement comprising a stent component having at least one section defining an at least partially conical body. The device further has a plurality of valve leaflets. An inner skirt is disposed within the stent component overlapping said at least partially conical body to define a conduit therewithin. An outer skirt is disposed outside the stent component overlapping only a portion of said at least partially conical body.

The inner skirt and/or the outer skirt are preferably made of pericardium tissue, most preferably porcine pericardium tissue.

Another aspect of the invention provides a valve replacement device comprising a stent component that is radially compressible to a compressed state for delivery and radially expandable to a functional state. The stent component may comprise at least one (and preferably a plurality) of attachment elements for cooperating with a stent-holder of a delivery device. Each attachment element (or at least one of the attachment elements) may comprise a U-shape portion joining two stent struts. The term U-shape is used herein to include any shape including a generally arcuate apex, whether or not the sides are straight or curved, bulged outwardly, parallel or non-parallel. In the compressed state of the stent when received within an accommodation region of the delivery catheter, the struts may lie adjacent each other at the attachment element, such that the arc of the U-shape portion extends around a first angle more than 180 degrees to define, for example, a closed or near closed (e.g. horseshoe shape) eyelet having an aperture larger than the spacing of the struts. The horseshoe shape of the eyelet aperture and the adjacent space between the struts may optionally together define a keyhole type shape. In an expanded (or non-collapsed) state of the stent when released from the accommodation region of the delivery catheter, the struts may move apart, and the arc of the U-shape portion may extend around a second angle that is less than the first angle, to at least partly open the eyelet further. For example, the second angle may be about 180 degrees or less. In the expanded state, the attached element may define a substantially non-horseshoe U-shape, for example, a straight-sided U-shape with an arcuate apex.

A delivery device for use with a valve replacement device as aforesaid may comprise a sent-holder provided within an accommodation region. The stent-holder may comprise (i) a projections receivable within each eyelet. The projection may be dimensioned such that, when the stent is in its collapsed state, the projection is trapped within the eyelet and unable to pass between the adjacent struts, and/or (ii) one or more recesses or interstices for accommodating the attachment element substantially therewithin, at least in the collapsed state of the stent.

The above forms can provide for a compact, yet reliable and self-opening and/or self-releasing attachment between a valve replacement device and a delivery device.

Another aspect of the present invention provides a valve replacement device comprising a stent component supporting at least two leaflets. The leaflets may be of pericardium tissue, most preferably porcine pericardium tissue or bovine pericardium. As mentioned previously, porcine pericardium may provide desirable tissue thinness. Bovine pericardium may be slightly thicker but more durable.

Each valve leaflet may include at least two tabs. The tabs may serve for supporting the leaflets relative to the stent component.

In some embodiments, the tabs may be attached directly to commissural supports (e.g. posts) of the stent component.

The tabs may attach to attachment means provided on the commissural support. For example, a tab may pass through an opening (e.g. a slot or slit) in a commissural support, from an interior of the stent component to an exterior. The portion of the tab exterior to the stent component may be folded to lie against the commissural support and/or sutured to the commissural support. Optionally respective tabs of two adjacent leaflets that meet at the commissural support pass through the same opening. Each tab may be folded to lie against the exterior of the commissural support without overlapping the other tab. The two tabs optionally are not directly attached to each other.

Additionally or alternatively, the leaflets may be attached to an inner skirt. The leaflets may be attached to an interior portion of the inner skirt, the tabs passing through openings (e.g., slots or slits) in the inner skirt to the exterior of the inner skirt. The inner skirt may have scalloped clearances, each such clearance being spanned by a respective leaflet. The inner skirt may have commissural portions or upstands in which the openings (e.g., slots or slits) are provided.

Additionally or alternatively, the material defining the inner skirt may include integral extension portions (e.g. flaps) that wrap around at least a portion of the commissural supports, for covering portions of the commissural supports and/or for covering the leaflet tabs secured to the commissural supports. The extension portions may be sutured to the commissural supports.

In some embodiments, a combination of any two or all three of the above arrangements may be used. For example, a pair of tabs of adjacent leaflets may pass through an opening in the inner skirt, and through an opening in the commissural support. The two openings may generally be in register. The tabs may be folded back in opposite directions, and sutured to the exterior of the commissural support (optionally without the tabs being sutured directly to each other). One or more flaps or extensions of the inner skirt at the commissural support may be wrapped around the exterior of the commissural support to cover the tabs and/or the commissural support. The extension(s) may be sutured to the commissural support. Optionally, the sutures may pass through the same suture holes in the commissural support as those used for attaching the tabs. The extension(s) may extend axially beyond the tab(s), such that the edges of the tabs are shrouded and protected.

Another aspect of the invention provides a valve replacement device comprising a stent component that is radially compressible to a compressed state for delivery and radially expandable to a functional state, a plurality of valve leaflets mounted within the stent component, an inner skirt attached to the valve leaflets, the inner skirt extending at least partly within the stent component, and an outer skirt extending at least partly outside the stent component.

In some embodiments, the outer skirt may extend further towards an inflow extremity of the stent component than does the inner skirt. Additionally or alternatively, the inner and outer skirts may partly overlap, at least with respect to the surface of at least one of the skirts. Additionally or alternatively, the inner and outer skirts may not have any coterminous extremity. Additionally or alternatively, the inner skirt may extend further towards an outflow extremity of the stent component than does the outer skirt.

At least a portion of the stent component over which at least one of the skirts extends, may optionally comprise a lattice structure having at least one row of a plurality of cells.

A function of the inner skirt may be to define a conduit within the stent to channel blood towards the valve leaflets, and obstruct leakage of blood through interstices of the stent component (e.g., lattice intertices). A function of the outer skirt may be to provide a seal surface outside the stent component for sealing with surrounding tissue, to obstruct leakage at the interface with surrounding tissue. Providing both skirts may be beneficial in terms of obstructing leakage overall. However, the presence of both skirts can add significantly to the thickness of material carried by the stent, and thereby increase the difficulty of compressing the stent-valve to a desirably small size. By providing both skirts, with only partial overlap in an axial direction, the benefits of both skirts can be obtained, but with a reduced thickness profile in the regions where only one skirt extends. Overlapping the skirts can provide better sealing between the skirts than were the skirts to be arranged edge to edge on the interior and exterior respectively of the stent component (for example, especially bearing in mind that the stent-valve is to be deformed substantially by compression for delivery and re-expansion at implantation).

The degree of skirt overlap in the axial direction may, for example, by at least 1 mm, or at least 2 mm, or at least 3 mm, or at least 4 mm, or at least 5 mm, or at least 6 mm, or at least 7 mm, or at least 8 mm. Additionally or alternatively, the degree of skirt overlap in the axial direction may, for example, be less than 10 mm, or less than 9 mm, or less than 8 mm, or less than 7 mm, or less than 6 mm, or less than 5 mm, or less than 4 mm. For example, the degree of skirt overlap in the axial direction may be about 4-6 mm.

At least one of the skirts (optionally each skirt) may extend a non-overlapped axial distance of at least 1 mm away from the region of overlap. The non-overlapped distance for the or each skirt may, for example, be at least 2 mm, or at least 3 mm, or at least 4 mm or at least 5 mm or at least 6 mm, or at least 7 mm or at least 8 mm or at least 9 mm, or at least 10 mm.

In some embodiments, the inflow edge or mouth of the stent component may have a zig-zag shape defined by a lattice structure of at least one row of cells. The zig-zag shape may be defined an alternating sequence of free apexes (e.g., at or defining an inflow extremity), and connected apexes (e.g. connected to lattice structure extending away from the inflow end towards the outflow end). In some embodiments, the inner skirt may extend only to the connected apexes. The outer skirt may overlap the inner skirt and extend further than the inner skirt, to a level corresponding to at least some of the free apexes.

In some embodiments, the inner skirt may extend towards the inflow extremity of the stent component. The outer skirt may overlap only partly the inner skirt while remaining spaced from an uppermost edge of the inner skirt. The outer skirt may extend towards (or optionally to) the inflow extremity of the stent component. The outer skirt may optionally not overlap (e.g., directly or indirectly through the stent component) any portion of the leaflets.

The inner skirt and/or outer skirt may be of any suitable material, such as pericardial tissue (e.g. porcine pericardium for thinness), PET, Dacron, etc. The inner and outer skirts may optionally be made of the same material as each other.

Another object of the present invention is to provide a delivery system for delivering a device for heart valve replacement. The delivery system comprises a flexible tubular catheter including a proximal end (or portion) and a distal end (or portion) with connection means (e.g. a stent holder). The delivery device further includes a device for heart valve replacement as described hereinabove. The delivery device is connected with said connection means such that the portion of the device adapted to be placed in or towards the ventricle is oriented towards the distal end of said catheter and the portion of said device adapted to be placed in the aorta is oriented toward said proximal end. In connection with the delivery device, the term "distal" means oriented away and the term "proximal" means oriented towards an operator of the delivery device.

The proximal end of the tubular catheter preferably includes a handle member for an operator. The distal end of the tubular catheter comprises connection means (e.g. stent holder) for releasably connecting a valve replacement device according to the present invention. The connection means may be of any suitable type. Preferably, the connection means are configured as pins or other projections that mate with corresponding attachment elements (e.g. hooks and/or eyelets) on the valve replacement device. Upon expansion of the stent component of the replacement device, the attachment elements are released from the pins, thus uncoupling the device from the tubular catheter.

The orientation of the valve replacement device on the tubular catheter allows the insertion of the device along an artery of a patient, preferably along the femoral or the subclavian artery. An arterial insertion is beneficial for some patients, as the procedure is less traumatizing than a surgical procedure. If desired, the tubular catheter may also be configured for transapical insertion.

According to still another aspect of the invention there is provided a method of replacement of a heart valve. A delivery device as disclosed above is inserted in a compressed state to the site of a heart valve to be replaced. The sent element is then expanded. The delivery device is optionally inserted by means of a flexible tubular catheter along an artery, preferably a femoral artery or a subclavian artery. Alternatively the delivery device is inserted transapically into a ventricle of the heart.

It is another objective of the present invention to provide a method of producing a valve replacement device having a reduced size when radially compressed which is quick and easy to perform. This objective is met by a manufacturing method as defined in the appended claims.

In some embodiments, in a first step of the method of production of a valve replacement device according to the present invention, a tubular skirt, preferably made of pericardium tissue, is provided. The term "tubular" has to be understood as to also encompass skirts which are generally shaped like a cylinder or a conical frustum. It also comprises skirts having elliptical cross sections, varying radii along an axis and the like. The tubular skirt preferably is made of porcine pericardium tissue.

In a next step, at least two leaflets, preferably also made of pericardium tissue are arranged adjacent to each other around the tubular skirt. The size of the leaflets is thereby selected such that once the leaflets are each arranged adjacent to each other, they span around the entire circumference of the tubular skirt. The lateral edges of said leaflets are thereby in contact at least in the area of their upper free edge.

The leaflets may be cut out of pericardium tissue. The leaflets include a free edge which is optionally curved. The curvature ay be a convex curvature. The size of the leaflets as well as the curvature of the free edge are thereby chosen in such a way as to allow the free edges to sealingly contact each other (e.g. coapt) when the stent component is in the functional state. The leaflets further include two lateral edges tapering towards a lower edge of the leaflet. The lower edge is shorter than the free edge. Preferably, said lower edge is also curved, more preferably with a convex curvature. The term "convex" is understood to define the curvature of an edge of the leaflet in relation to the surface of the leaflet. Therefore, a convexly curved edge bulges out of the leaflet.

Prior to the cutting, the pericardium tissue is preferably treated to avoid any shrinkage of the leaflets at a later stage.

The lateral edges and the bottom edge of the leaflets are then attached onto the surface of the tubular skirt, preferably by means of a suture. Alternatively, the leaflets may also be attached by other means, such as gluing or the like. The free edges must remain unattached to the skirt, as they will form the replacement valve in the assembled valve replacement device.

In the next step, the tubular skirt is everted, so that the leaflets now lie inside the generally tubular conduit of the tubular skirt. The everted skirt is then finally attached to a stent component.

As the valve component of a valve replacement device produced according to the method of the present invention is made "inside out", the attachment of the leaflets to the skirt is much easier and requires lesser steps.

To further reduce the size of the crimped valve replacement device, at least some skirt tissue overlapping the leaflets is preferably removed. This may be done by cutting the skirt along the suture attaching the leaflets to the skirt. The removal of the tissue is preferably performed using scissors or a scalpel. This allows to further reduce the diameter of the valve replacement device, as, with the exception of the area of sutures, only one layer of tissue is present. Removal of such skirt tissue creates scalloped clearances in the skirt tissue, spanned by the leaflets. The skirt tissue may include commissural portions where neighboring leaflets meet. The commissural portions may include circumferential and/or axial extensions (e.g. flaps) for providing protective wrap material for wrapping around the exterior of a commissural post of a stent component.

The at least two leaflets preferably additionally comprise at least two tabs, preferably one tab is thereby arranged on each lateral edge of each leaflet, most preferably in the area of said free edge. Alternatively, the at least two leaflets may comprise more tabs, e.g. two tabs on each lateral edge of each leaflet. After eversion of the tubular skirt, at least two slits are cut into the skirt and at least one tab is inserted through each slit. Alternatively, two tabs of adjacent leaflets are inserted through the same slit. This allows to pass the tabs from the inside of the skirt to the outside.

The tabs are then preferably directly attached to the stent component, preferably to attachment means provided on the stem of a wishbone shaped commissural post, most preferably by pulling said tabs through openings provided on said commissural posts, followed by suturing said tabs to said commissural posts. Superfluous material of said tabs may then be removed.

The extensions of the commissural portions of the skirt material may be wrapped around the commissural posts without passing through the same openings as the tabs.

Preferably, said tubular skirt is made by wrapping a generally rectangular piece of pericardium having an appropriate size around a mandrel having a size and form corresponding to the intended size and form of the valve component of the valve replacement device. The piece of pericardium is then stitched together such as to yield a generally tubular skirt. The pericardium is then preferably treated to cause shrinkage of the tissue, whereby the annular skirt will adopt the form of the outer contour of the mandrel. The mandrel may therefore additionally impart a specific shape to the annular skirt. In a especially preferred embodiment, said mandrel will impart a circumferential bulge on said skirt. During attachment of said at least two leaflets to said annular skirt, the annular skirt may remain on said mandrel.

Further, said flaps of the skirt material may be wrapped over said tabs and said openings, such as to cover the suture holding the tabs on said commissural posts. This further protects the valve replacement device from any damage when crimping the device to less than 18 French in diameter.

While certain aspects of the invention have been defined above and/or in the appended claims, protection is claimed for any novel feature or idea described herein and/or illustrated in the drawings, whether or not emphasis has been placed thereon.

Further advantages and characteristics of the present invention are described in the following description of examples and figures.

Figure 2:
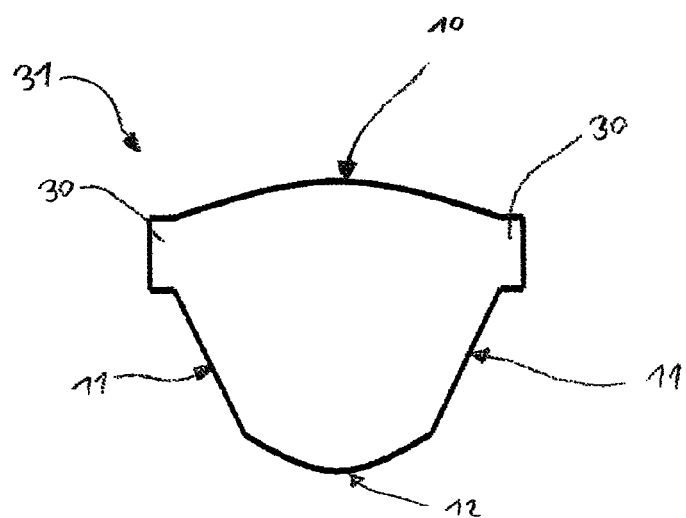
Figure 3:
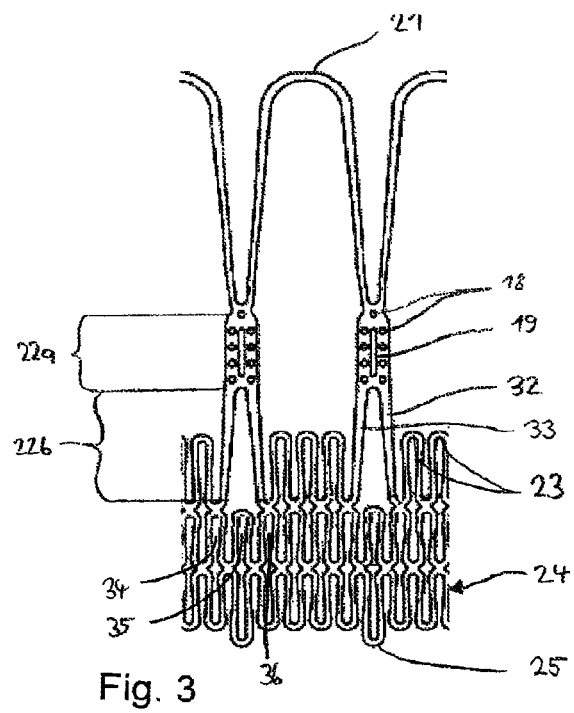
Figure 4A:
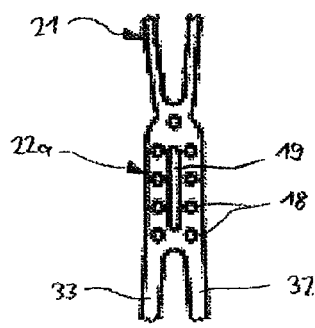
Figure 4B:
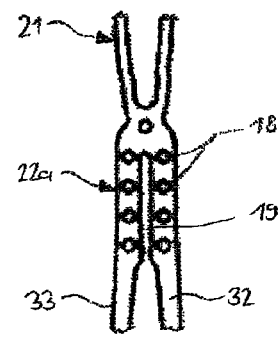
Figure 4C:
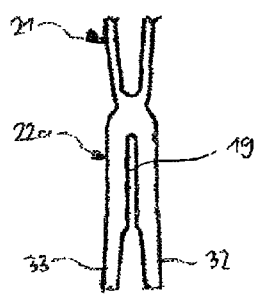
Figure 4D:
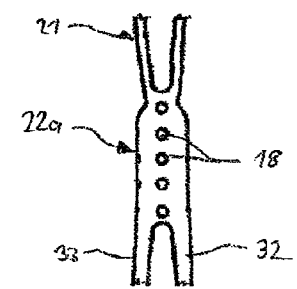
Figure 6:
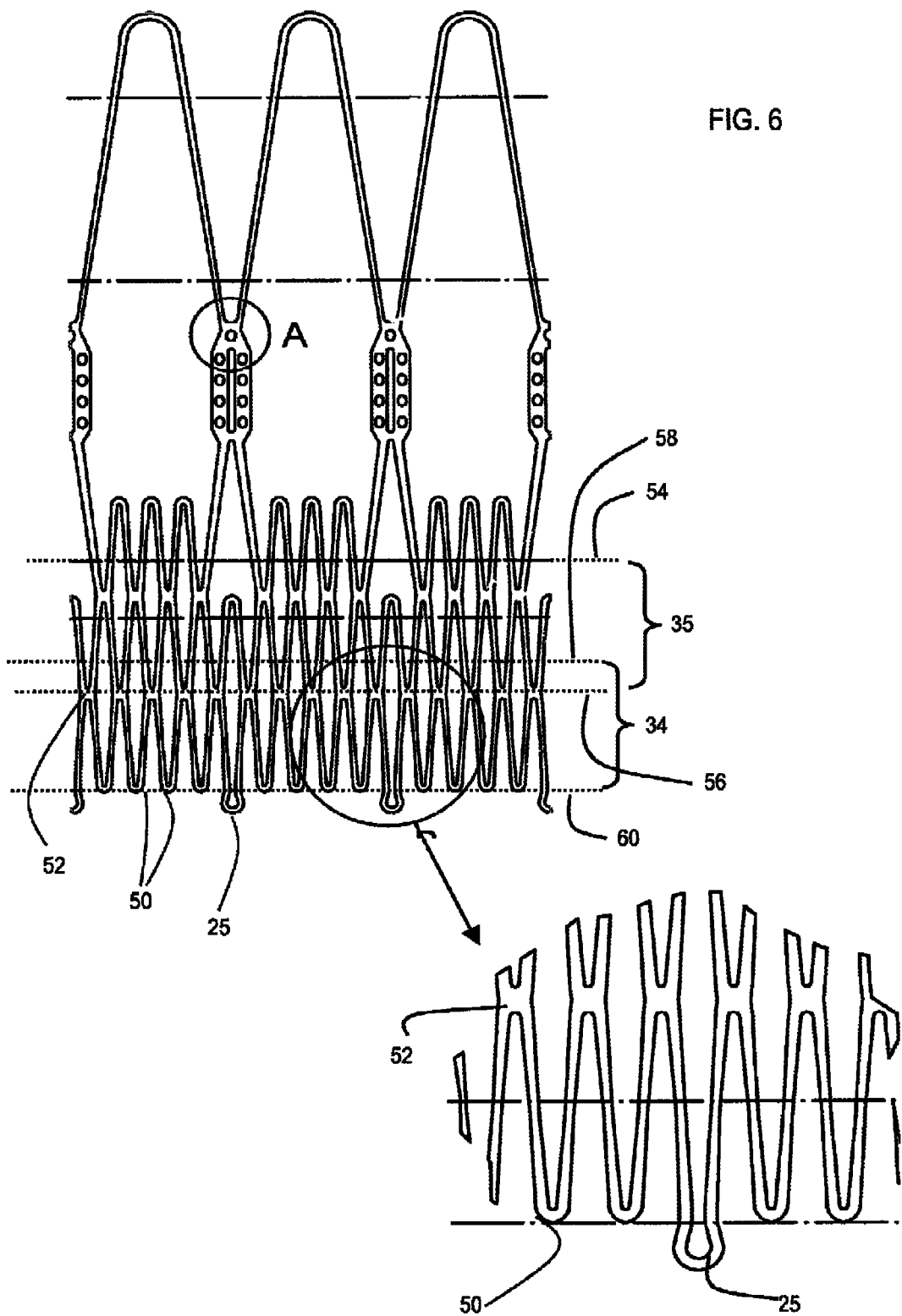

FIG. 1: Shows an exemplary embodiment a valve replacement device according to the present invention;

FIG. 2: shows a leaflet of a valve component according to the present invention;

FIG. 3: shows a detailed view of commissural posts having a wishbone shape;

FIG. 4a-d: are representations of different configurations of attachment means for the tabs of the leaflets;

FIG. 5a-e: shows a method of producing a valve replacement device according to the present invention;

FIG. 6: shows an alternative embodiment of stent component, in a view similar to FIG. 3;

FIG. 7: shows a schematic view of a delivery device for the valve replacement device;

FIG. 8: shows a schematic close-up showing the relation between a stent holder and attachment element when the stent component is in its compressed condition; and FIG. 9: shows schematically the attachment element when the stent component is expanded to its functional state.

FIG. 1 shows a preferred embodiment of a valve replacement device 15 according to the present invention. The valve replacement device 15 is adapted to be inserted by a transfemoral approach, but the device may also be inserted generally by another transvascular approach or by a transapical approach. The replacement device 15 has a first end 26, a second end 27 and an intermediate section 17 and comprises a stent component 20 and a valve component 5. In this embodiment, the first end 26 is intended to be positioned in an artery, while the second end 27 is intended to be positioned in or towards the ventricle of the heart of a patient. When the valve replacement device 15 is in place, blood will flow from the second end 27 to the first end 26 via the intermediate section 17. Therefore, the section between the second end 27 and the intermediate section 17 is also referred to as "inflow section". Accordingly, the section between the intermediate section 17 and the second end 26 is referred to as "outflow section".

The stent component 20 comprises stabilization arches 21, commissural posts 22, upper anchoring crown 23, lower anchoring crown 24 as well as attachment elements 25. The configuration of the stent component is thereby similar to the configuration as described in the co-pending application EP 2 205 183. The stabilization arches 21 serve to stabilize the stent 15 in a blood vessel, preferably the aorta, during deployment. The arches 21 are attached with their proximal end directly to an upper, i.e. distal end of the commissural posts 22. Starting from the proximal end the arches 21 diverge radially outwardly over a part of their length and converge radially inwardly towards their distal end. The terms "distal" and "proximal" are used hereunder to designate the parts of the valve replacement device 15 or of its components lying further away or closer to the heart, respectively. The distal end sometimes is also referred to as the aortic end and the proximal end as the ventricular end.

Three leaflets 31 of a replacement heart valve are attached to the commissural posts 22. The leaflets 31 are formed from porcine pericardium tissue. The upper anchoring crown 23 serves to attach the stent 15 to the aortic side of a heart valve, while the lower anchoring crown 24 serves to attach the stent 15 in the native annulus, or towards the ventricular side of the heart valve. Attachment means 25 enable the removable attachment of the stent 15 to a delivery device.

The commissural posts 22 have an axial length L2 corresponding substantially to the axial length L1 of the stabilization arches 21. Typically the length L1 is about 90% to 110% of the length L2. The commissural posts 22 have a wishbone shape and each include an upper part 22a for direct fixation of tabs 30 of valve leaflets 31 and a lower part 22b with two legs or arms 32, 33. The tabs 30 are fixed to the upper part 22a by wrapping around and suturing. Lateral sides of the leaflets 31 are sutured directly or indirectly to the two arms 32, 33 of the lower part 22b. The lower crown 24 is formed by a substantially tubular portion having a lattice structure of cells 34, 35, 36. The two arms 32, 33 of each wishbone shaped commissural post 22 span a respective sequence of at least three adjacent cells 34, 35, 36. The wishbone extends from outer cells 34, 36 of the sequence without attachment to at least one intermediate cell 35 of the sequence.

The lower, i.e proximal end of the stent is covered by an outer skirt 34 extending axially along about half of the height of the cells 34, 35, 36. On the inner side of the stent 15 there is an inner skirt 35 preferably made of pericardium material sealing the space between two neighbouring arms 32, 33 of a wishbone shaped commissural post 22.

FIG. 2 is a representation of a leaflet 10 according to the present invention. A free edge 10 is configured such as to sealingly engage free edge 10 of at least one further leaflet 31 to form a tightly closing valve. Preferably, the free edge 10 is arcuate, although a straight edge may also be used. The leaflet further includes two lateral edges 11 and a lower edge 12. The lower edge 12 is arcuate, while the lateral edges 11 are linear. The surface framed by the lateral edges 11 and the lower edge 12 is frequently referred to as "belly" of the leaflet 31. Two tabs 30 are arranged on both lateral edges 11 in the area of the free edge 10. The tabs 30 are sized and shaped such as to be insertable into attachment means provided on commissural posts of the stent component of a valve replacement device (see also FIGS. 3 and 4). At least two leaflets 31 are positioned in such a device to form a valve component, but preferably the valve component comprises three leaflets 31.

FIG. 3 shows a detailed view showing the configuration of a stent component 20 having commissural posts 22 in a wishbone shape. The stent component 20 is shown in its collapsed, i.e. crimped state. The upper parts 22a of commissural posts 22 are joined together by stabilization arches 21. Further, these upper parts 22a comprise fixation means for tabs 30 of leaflets 31, here represented by openings 19 and holes 18. The lower part 22b of commissural posts 22 comprises two arms 32, 33. The commissural posts 22 thereby have an overall wishbone shaped configuration. As can be readily seen on this figure, both arms 32, 33 of commissural posts 22 span a sequence of three consecutive cells 34, 35, 36 of the lower crown 24. The arms 32, 33 are thereby connected to the outer cells 34, 36 of the sequence without attachment to the intermediate cell 35 of the sequence. The lower crown 24 further comprises attachment elements 25 in the form of hooks. These attachment elements 25 allow the removable attachment of the valve replacement device 15 to a delivery device.

FIG. 4 shows different configuration of attachment means on the upper part 22a of commissural posts 22. The configuration shown in FIG. 4a corresponds to the configuration of the commissural posts 22 as shown on FIG. 3. An opening 19 in the form of a long hole is arranged in the centre of the upper part 22a. The opening 19 is shaped and sized such as to allow insertion of at least one tab 30. However, the size of the opening 19 is preferably such that two tabs 30 may be inserted. Further, the opening 19 is flanked on both sides by four holes 18. A further hole 18 is arranged on top of the opening 19. The holes 18 are intended to accommodate suture wire used to attach the tabs 30 to the commissural posts 22. An alternative configuration of the opening 19 is shown on FIG. 4b. In this embodiment, the opening 19 is configured as longitudinal slit in the middle of the upper part 22a. Again, the opening 19 is flanked by holes 18. FIG. 4c shows a further embodiment without any holes 18. The opening 19 is shown as longitudinal slit, but may alternatively also be configured as long hole. In this embodiment, tabs are inserted through opening 19, folded back towards the leaflet 31 and sutured thereto. A further alternative embodiment is shown on FIG. 4d. In this embodiment, the attachment means only comprise holes 18. A tab 30 is thereby folded backward onto the leaflet 31 and sutured thereto. A further suture is sewn from the fold of the tab 30 into the openings 18, thereby attaching the tabs 30 to commissural posts 22.

FIG. 5 represents a method of producing a valve replacement device 15 according to the present invention. FIG. 5a shows the first step of the method. A generally rectangular piece of pericardium tissue 2 having an appropriate size is wrapped around a mandrel 1 having an appropriate shape. The mandrel preferably comprises specific shape elements, here exemplarily shown as bulges 4 to be imparted to the inner skirt of the valve replacement device. The pericardium tissue is then sewn together with suture 3 and optionally treaded to impart some shrinkage of the tissue. In the next step, shown on FIG. 5b, at least two but preferably three tabs 31 are arranged around said piece of pericardium tissue 2 on its outside surface. The tabs 31 are thereby arranged such that tabs 30 of neighbouring leaflets 31 are at the same height along the longitudinal axis of the mandrel 1. Further, neighbouring leaflets 31 contact each other at their lateral edges in the area of the tabs 30. The leaflets 31 are then sewn to the pericardium tissue 2 along the lower edge 12 and the lateral edges 11. The tabs 30 remain free. Thereafter, the pericardium tissue 4 is removed from the mandrel 1 and everted (see FIG. 5c). The leaflets 31 are now located on the inside of the cylindrically shaped pericardium tissue 4. Excess material 6 of the pericardium tissue is removed, e.g. by cutting. At least a portion of the pericardium tissue 4 located on the exterior of the leaflets 31 is also removed along suture 7 which connects the pericardium tissue 4 with the leaflets 31. At the area of the tabs, slits 8 are provided in the pericardium tissue 4 which are arranged and sized such as to be able to pass tabs 30 therethrough. At the area of the slits 8, two flaps 9 of the pericardium tissue 4 are left. The tabs 30 are then passed through the slits 8. The now finished valve component 5 includes inner skirt 28 and leaflets 31. With the exception of the area around suture 7, the valve component 5 consists of a single layer of pericardium tissue. In a next step shown on FIG. 5d, the valve component 5 is inserted into the stent component 20. The tabs 30 are inserted through the openings 19 located on the commissural posts 22, folded back toward leaflets 31 and further attached to the commissural posts 22 by suturing. The suture stitches are passed through holes 18. Superfluous material of the tabs 30 is subsequently removed. Then, the flaps 9 are folded over the upper part 22a of the commissural posts 22 to cover the suture of the tabs 30, thus forming a kind of sleeve around the upper part 22a of the commissural posts 22. FIG. 5e shows the finished valve replacement device 15. The valve component 5 is additionally attached to the stent component 20 by means of sutures 13 in the area of the arms 32, 33 of each wishbone shaped commissural posts 22. Further, the inner skirt 28 is attached to the cells of the lower crown 24 by means of sutures 14. The lower crown 24 may additionally be covered on the outside by an outer skirt 29, as shown on the embodiment of FIG. 1.

In some embodiments, the flaps 9 may have an axial extent that is greater, in the inflow and/or outflow direction, than the tabs 30. When the flaps 9 are folded around the commissural post, the flaps 9 may extend axially beyond the edge of the tabs 30, thereby covering and protecting the tabs 30. As can be seen in FIG. 5e, the flaps 9 may extend axially above the level of the leaflets.

FIG. 6 illustrates schematically a modified arrangement of stent component, and a modified arrangement of inner skirt 35 and outer skirt 34. The inflow end or mouth of the stent component has a zig-zag shape defined by cells of a lattice structure including at least one row of lattice cells. The zig-zag shape is defined by alternating free apexes 50 and connected apexes 52. The free apexes 50 define an inflow extremity. The connected apexes 52 communicate with adjacent cells in the row.

The position of the inner skirt 35 is indicated by lines 54 and 56, and extends from the commissural posts and/or leaflets towards the inflow extremity. The line 54 indicates generally the level of the lower edges of the leaflets, although it is to be appreciated that the inner skirt 35 may have commissural portions that extend axially up the commissural posts of the stent component. The position of the outer skirt 34 is indicated by lines 58 and 60 and extends further than the inner skirt 35 towards the inflow extremity.

In the illustrated example, as indicated by the line 56, the inner skirt 35 extends to a level corresponding to (at least some of) the connected apexes 52. The outer skirt 34 extends to a level corresponding to (at least some of) the free apexes 50.

The outer skirt 34 may have a zig-zag shaped edge that matches substantially the zig-zag shape of the inflow edge.

The inner skirt 35 extends further than the outer skirt 34 in the opposite direction towards the outflow end (and/or extremity) of the stent. The inner and outer skirts may partly overlap each other in the axial direction. The degree of axial overlap may, for example, be at least 1 mm, or at least 2 mm, or at least 3 mm, or at least 4 mm, or at least 5 mm, or at least 6 mm, or at least 7 mm, or at least 8 mm. Additionally or alternatively, the degree of skirt overlap in the axial direction may, for example, be less than 10 mm, or less than 9 mm, or less than 8 mm, or less than 7 mm, or less than 6 mm, or less than 5 mm, or less than 4 mm. For example, the degree of skirt overlap in the axial direction may be about 4-6 mm.

As can be seen in FIG. 6, at least some of the cells have an exposed free apex 50a that extends beyond the free apexes 50 of adjacent cells in the row, and is not covered by the outer skirt 34. The exposed free apexes 50a provide attachment elements 25 for engaging a stent holder of a delivery device.

Also as can be seen at the circle A in FIG. 6, and the corresponding area in FIG. 3, suture bores may be provided along each side of the opening in the commissural post, and at only one axial end of the stem. Such an arrangement can enable the size of the stem of the commissural post to be reduced compared to an arrangement in which suture bores might be provided at both axial opposite ends.

FIG. 7 illustrates schematically a delivery device 62, e.g. delivery catheter, for inserting the valve replacement device at the heart. The catheter may be advanced over a guidewire (shown by the broken line). The catheter comprises a distal portion 64 for insertion into the anatomy and having an accommodation region for accommodating the valve replacement device in its compressed state. A stent holder (described below) is provided at the accommodation region for restraining the valve replacement device against axial movement until the stent component expands to its functional state, whereupon the stent component detaches from the stent holder. The distal portion 64 may also include a sheath arrangement for constraining the stent-component in its compressed state for delivery, the sheath arrangement being operable to unsheath the stent component to allow the stent-component to expand to its functional state. The delivery catheter 62 further comprises a stem portion 66, which is optionally flexible, extending towards a proximal portion 68 having a control handle.

Different examples of attachment elements 25 are envisaged. Generally, each attachment element 25 may be defined by an apex joining first and second struts that extend from an end of the stent component. The struts may be members defining a lattice or skeletal stent structure of the stent-valve 10. In the case of a lattice, the cell associated with the struts may project axially beyond neighbouring cells of the lattice.

In FIG. 3, the struts may extend generally linearly to meet at an apex defining a generally straight-sided U-shape in the compressed state (illustrated in FIG. 3), and expanding to a V-shape when the stent component expands to its functional state. In FIG. 6, the apex is slightly different by having a generally rounded or horseshoe U-shape when in the compressed state (illustrated in FIG. 6), and expanding to a generally non-horseshoe shape, e.g. to a straight sided U-shape (FIG. 9), when the stent component expands to its functional state.

Referring to FIG. 8, the stent holder 78 may generally comprise a plurality of projections 84 and/or interstices 86 for accommodating the attachment elements 25 of FIG. 3 and/or FIG. 6. The edge 90 of each interstice 86 may optionally be rounded or chamfered. The projections 84 may be configured for fitting within the interior of the apex of each attachment element 25, when the stent component is in its collapsed state. The engagement between the projection 84 and the attachment element restrains the attachment element (and hence the stent-valve 10) against axial movement, at least in an axial direction away from the stent holder 24, and optionally in both axial directions.

In the case of a self-expanding stent component, the attachment elements 25 may disengage when the portion of the stent component from which the attachment elements 25 extend, is uncovered by the sheathing arrangement of the delivery catheter. Upon expansion of the stent component, the struts move apart to open the U- or V-shape of the attachment element apex. As the apex opens, this enlarges the interior of the attachment element 25 to facilitate disengagement between the projection 84 and the attachment element 25. The chamfered edge 90 of the interstice 86 also acts as a ramp surface to "lift" radially the struts out of the clearance 88 as the struts expand circumferentially and bear against the edge 90. In case the attachment elements 25 may stick accidentally within the interstice 86, the attachment elements 25 may be freed by slight rotation and/or axial displacement of the catheter, to promote further riding against the edge 90.

In the specific example of FIGS. 6, 8 and 9, the projections 84 are fingers or pins, suitable for fitting within the interior of the horseshoe shape of the attachment element. The projections may be generally radially projecting, or may be inclined at an angle away from the stent component, for example, at an angle of up to about 10 degrees (e.g. about 5 degrees). In a collapsed state of the stent component (FIGS. 6 and 8), the struts may lie closely adjacent each other at the attachment element 25, such that the arc of the U-shape portion 25 extends around a first angle more than 180 degrees to define a closed or near closed eyelet having an aperture larger than the spacing of the struts, to accommodate the pin 84. The eyelet aperture and space between the struts may together define a keyhole type shape. Alternatively, the struts may bear against each other at the attachment element 25 to close the eyelet. Either arrangement can restrain the attachment element 25 in both axial directions, merely by engagement between the attachment element 25 and the projection 84. This may be advantageous by enabling a larger chamfer surface to be used at the edge 90 of the interstice 86 and/or at the end face 92 of the stent-holder. A chamfered end face 92 may be desirable to facilitate withdrawal of the stent holder 78 through the valve replacement device once implanted. The arrangement also allows the struts of the attachment element to be compressed close together, such that the provision of the attachment element does not impede compressing the stent component to a desirably small size.

Optionally, the interstice 86 is closed at one axial end, to provide additional protection against the attachment element 25 displacing axially in a direction that would force the projection 84 into the space between the struts.

Referring to FIG. 9, in the expanded (or non-collapsed) functional state of the stent component, the struts may move apart, and the arc of the U-shape apex may extend around a second angle that is less than the first angle, to at least partly open the eyelet. The second angle may be about 180 degrees or less. In a similar manner to that described above, opening of the apex may facilitate disengagement from the projection 84. The chamfered edge 90 of the interstice 86 also acts as a ramp surface to "lift" radially the struts out of the clearance 88 as the struts 70 and 72 expand circumferentially and bear against the edge 90.

It is emphasized that the foregoing description is merely illustrative of non-limiting preferred forms of the invention. Many modifications and equivalents may be used within the scope of the invention.

The invention claimed is:

1. A valve replacement device for transcatheter implantation, comprising:
   a stent component having an inflow extremity and an outflow extremity,
   the stent component being radially compressible to a compressed state for delivery to a site of implantation and radially expandable to a functional state;
   valve leaflets mounted at least partly within the stent component;
   an inner skirt attached to the valve leaflets, the inner skirt extending at least partly within the stent component towards the inflow extremity; and
   an outer skirt extending at least partly outside the stent component, the outer skirt extending further than the inner skirt towards the inflow extremity wherein the stent component comprises a first end, a second end and at least one intermediate section arranged between the first end and the second end, the intermediate section comprising at least two commissural posts; and each valve leaflet includes at least two tabs, the tabs projecting through slits in the inner skirt and attached directly to the commissural posts.

2. The device of claim 1, wherein the inner skirt and the outer skirt partly overlap in an axial direction.

3. The device of claim 1, wherein the inner skirt extends further than the outer skirt towards the outlet extremity of the stent component.

4. The device of claim 1, wherein a mouth of the stent component has a zig-zag shape defined by a lattice structure of at least one row of cells, the zig-zag shape being defined by an alternating sequence of free apexes at the inflow extremity and connected apexes connecting to adjacent cells, the inner skirt extending only to a level corresponding to at least some of the connected apexes, and the outer skirt extending to a level corresponding to at least some of the free apexes.

5. The device of claim 1, wherein the row of cells at the mouth of the stent component includes at least first and second cells having an exposed free apex that extends beyond the free apexes of adjacent cells in the row and is not covered by the outer skirt, the exposed free apexes providing attachment elements for engaging a stent-holder of a delivery device for delivering the valve replacement device to a site of implantation.

6. The device of claim 1, wherein the stent component comprises a first end, a second end and at least one intermediate section arranged between the first end and the second end, the intermediate section comprising at least two commissural posts each in the shape of a wishbone including a stem communicating with adjacent stent structure and two legs communicating with adjacent stent structure, and each valve leaflet includes at least two tabs directly attached to the commissural posts.

7. The device of claim 6, wherein the stent component comprises a lattice structure having at least one row of cells arranged between the intermediate section and the second end, the wishbone shape of each commissural post spanning a respective sequence of at least three adjacent cells such that the wishbone extends from outer cells of the sequence without attachment to the at least one intermediate cell of the sequence.

8. The device of claim 6, wherein the legs of the wishbone shaped commissural posts are shaped such as to match the lateral edges of the leaflets.

9. The device of claim 6, wherein the at least two commissural posts are connected together by at least two stabilization arches arranged between the first end and the intermediate section.

10. The device of claim 1, wherein tabs of two adjacent leaflets meet and project through the same slit in the inner skirt, and are attached directly to the same commissural post.

11. The device of claim 1, wherein each tab is attached directly to the commissural post by passing through a slot in the commissural post and/or being sutured to the commissural post.

12. The device of claim 1, wherein the leaflets are attached to the inner skirt, the inner skirt having commissural portions spaced by scallop-shaped clearances, each clearance spanned by a leaflet, and wherein each commissural portion of the inner skirt comprises at least one flap that is folded at least partly around a respective commissural post.

13. The device of claim 12, wherein each commissural portion of the inner skirt comprises two flaps that are folded at least partly around a respective commissural post.

14. The device of claim 12, wherein the at least one flap covers substantially a portion of the tab that is attached to the commissural post.

15. The device of claim 12, wherein the at least one flap extends axially beyond an edge of the tab that is attached to the commissural post.

* * * * *